(12) United States Patent
Jaramillo-Botero et al.

(10) Patent No.: US 9,090,936 B2
(45) Date of Patent: Jul. 28, 2015

(54) USING A FIELD EFFECT DEVICE FOR IDENTIFYING TRANSLOCATING CHARGE-TAGGED MOLECULES IN A NANOPORE SEQUENCING DEVICE

(71) Applicant: CALIFORNIA INSTITUTE OF TECHNOLOGY, Pasadena, CA (US)

(72) Inventors: Andres Jaramillo-Botero, Pasadena, CA (US); William A. Goddard, III, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 395 days.

(21) Appl. No.: 13/621,745

(22) Filed: Sep. 17, 2012

(65) Prior Publication Data

US 2013/0069665 A1 Mar. 21, 2013

Related U.S. Application Data

(60) Provisional application No. 61/536,327, filed on Sep. 19, 2011, provisional application No. 61/536,381, filed on Sep. 19, 2011.

(51) Int. Cl.
| | |
|---|---|
| *B82Y 15/00* | (2011.01) |
| *C12Q 1/68* | (2006.01) |
| *G01N 27/447* | (2006.01) |
| *G01N 33/18* | (2006.01) |

(52) U.S. Cl.
CPC ............... *C12Q 1/6869* (2013.01); *B82Y 15/00* (2013.01); *G01N 27/44704* (2013.01); *G01N 33/1826* (2013.01); *G01N 33/18* (2013.01)

(58) Field of Classification Search
None
See application file for complete search history.

(56) References Cited

U.S. PATENT DOCUMENTS

| | | | |
|---|---|---|---|
| 2003/0178617 A1* | 9/2003 | Appenzeller et al. | 257/20 |
| 2004/0007740 A1 | 1/2004 | Abstreiter et al. | |
| 2005/0170347 A1 | 8/2005 | Miyahara et al. | |
| 2007/0190543 A1* | 8/2007 | Livak | 435/6 |
| 2008/0032294 A1 | 2/2008 | Kawarada | |
| 2008/0063566 A1* | 3/2008 | Matsumoto et al. | 422/68.1 |
| 2008/0171316 A1* | 7/2008 | Golovchenko et al. | 435/6 |
| 2009/0136958 A1 | 5/2009 | Gershow et al. | |
| 2010/0084276 A1 | 4/2010 | Lindsay | |
| 2010/0327847 A1 | 12/2010 | Leiber et al. | |

(Continued)

FOREIGN PATENT DOCUMENTS

| | | | | |
|---|---|---|---|---|
| WO | WO 2009035647 A1 * | 3/2009 | | G01N 27/414 |
| WO | 2010/066794 | 6/2010 | | |

OTHER PUBLICATIONS

Vlassiouk et al, Proc. Nat. Acad. Sci., vol. 106, pp. 21039-21044 (2009).*

(Continued)

*Primary Examiner* — Robert T Crow
(74) *Attorney, Agent, or Firm* — Steinfl & Bruno LLP (57) ABSTRACT

A detector apparatus includes a field-effect transistor configured to undergo a change in amplitude of a source-to-drain current when at least a portion of a charge-tagged molecule translocates through the nanopore. In some implementations, the field-effect transistor is a carbon nanotube field effect transistor and the nanopore is located in a membrane. In other implementations, the field-effect transistor is a carbon nanotube field effect transistor and the nanopore is implemented in the form of a nano-channel in a semiconductor layer.

9 Claims, 8 Drawing Sheets

(56) References Cited

U.S. PATENT DOCUMENTS

| | | |
|---|---|---|
| 2011/0133255 A1 | 6/2011 | Merz |
| 2011/0168562 A1 | 7/2011 | Nuckolls et al. |
| 2011/0279125 A1 | 11/2011 | Bedell et al. |

OTHER PUBLICATIONS

1-Branton, D. et al., *The potential and challenges of nanopore sequencing*, Nature Biotechnology, Oct. 2008, vol. 26, No. 10, pp. 1146-1153.
2-Novoselov, K.S., et al., *Electric field effect in atomically thin carbon films*. Science, 2004, 306(5696): p. 666-669.
3-Chen, Z.H., et al., *Graphene nano-ribbon electronics*. Physica E-Low-Dimensional Systems & Nanostructures, 2007, 40(2): p. 228-232, (pp. 1-6).
4-Ikeda, T. et al., *Toward Electrochemically Controllable Tristable Three-Station [2] Catenanes*, Chem. Asian J., 2007, vol. 2, pp. 76-93.
5-Li, J.L., et al., *DNA molecules and configurations in a solid-state nanopore microscope*. Nature Materials, 2003, 2(9): p. 611-615.
6-Li, J., et al., *Nanoscale Ion-beam sculpting at nanometre length scales*. Nature, 2001, 412(6843): p. 166-169, (pp. 1-11).
7-Meller, A. et al., *Single molecule measurements of DNA transport through a nanopore*, Electrophoresis, 2002, vol. 23, pp. 2583-2591.
8-Dekker, C., *Solid-state nanopores*. Nature Nanotechnology, 2007, 2(4): p. 209-215.
9-Gorjizadeh, N. and Y. Kawazoe, *Chemical Functionalization of Graphene Nanoribbons*. Journal of Nanomaterials, 2010, (pps. 1-7).
10-Hugel, T., et al., *Single-molecule optomechanical cycle*. Science, 2002, 296(5570): p. 1103-1106.
11-Umapathy, N.B.S., *Early time dynamics of trans-azobenzene isomerization in solution from resonance Raman intensity analysis*. Journal of Chemical Physics, 1997, 107(19): p. 7849-7858.
12-Krapf, D., et al., *Fabrication and characterization of nanopore-based electrodes with radii down to 2 nm*. Nano Letters, 2006, 6(1): p. 105-109.
13-Zandbergen, H.W., et al., *Sculpting nanoelectrodes with a transmission electron beam for electrical and geometrical characterization of nanoparticles*. Nano Letters, 2005, 5(3): p. 549-553.
14-Merino, E., *Synthesis of azobenzenes: the coloured pieces of molecular materials*. Chemical Society Reviews, 2011, 40(7): p. 3835-3853.
15-Han, M., et al., *Light-driven molecular switches in azobenzene self-assembled monolayers: effect of molecular structure on reversible photoisomerization and stable cis state*. Chemical Communications, 2010, 46(20): p. 3598-3600.
16-Uchida, K., et al., *Photoinduced reversible formation of microfibrils on a photochromic diarylethene microcrystalline surface*. Angewandte Chemie-International Edition, 2006, 45(39): p. 6470-6473.
17Min, S.K., et al., *Fast DNA sequencing with a graphene-based nanochannel device*. Nature Nanotechnology, 2011, 6(3): p. 162-165.
18-Gillis, H.P., et al., *Low-Energy Electron-Enhanced Etching of Si(100) in Hydrogen Helium Direct-Current Plasma*. Applied Physics Letters, May 8, 1995, 66(19): p. 2475-2477.
19-Gillis, H.P., et al., *Patterning III-N semiconductors by low energy electron enhanced etching (LE4)*. Mrs Internet Journal of Nitride Semiconductor Research, 1999, 4: p. art. No.-G8.2.
20-Nguyen, T.D., et al., *Wafer-Scale Nanopatterning and Translation into High-Performance Piezoelectric Nanowires*. Nano Letters, 2010, 10(11): p. 4595-4599.
21-Maune, H.T., et al., *Self-assembly of carbon nanotubes into two-dimensional geometries using DNA origami templates*. Nature Nanotechnology, 2010, 5(1): p. 61-66, (pp. 1-6).
22-Park, J.Y., *Carbon nanotube field-effect transistor with a carbon nanotube gate electrode*. Nanotechnology, 2007, 18(9).
23-Svensson, J., et al., *A carbon nanotube gated carbon nanotube transistor with 5 ps gate delay*. Nanotechnology, 2008, 19(32).
24-Stokbro, K., et al., *Semiempirical model for nanoscale device simulations*. Physical Review B, 2010, 82(7), pp. 1-8.
25-Cerda, J. and F. Soria, *Accurate and transferable extended Huckel-type tight-binding parameters*. Physical Review B, 2000, 61(12): p. 7965-7971.
26-Beaucage, S.L. and M.H. Caruthers, *Deoxynucleoside Phosphoramidites—a New Class of Key Intermediates for Deoxypolynucleotide Synthesis*. Tetrahedron Letters, 1981, 22(20): p. 1859-1862.
27-Wind, S.J., et al., *Vertical scaling of carbon nanotube field-effect transistors using top gate electrodes* (vol. 80, p. 3817, 2002). Applied Physics Letters, 2002, 81(7): p. 1359-1359.
28-Chen, Z., et al., *Externally assembled gate-all-around carbon nanotube field-effect transistor*. IEEE Electron Device Letters, Feb. 2008, 29(2): p. 183-185.
29-Singh, S.K., et al., *LNA (locked nucleic acids): synthesis and high-affinity nucleic acid recognition*, Chemical Communications, 1998(4): p. 455-456.
30-Koshkin, A.A., et al., *LNA (Locked Nucleic Acids): Synthesis of the adenine, cytosine, guanine, 5-methylcytosine, thymine and uracil bicyclonucleoside monomers, oligomerisation, and unprecedented nucleic acid recognition*, Tetrahedron, 1998, 54(14): p. 3607-3630.
1-Restriction Requirement issued for U.S. Appl. No. 13/621,735, filed Sep. 17, 2012 in the name of Andres Jaramillo-Boteo. date issued: Sep. 11, 2014.
2-Non-Final Office Action issued for U.S. Appl. No. 13/621,735, filed Sep. 17, 2012 in the name of Andres Jaramillo-Boteo. date issued: Sep. 25, 2014.
3-Notice of Allowance issued for U.S. Appl. No. 13/621,735 filed Sep. 17, 2012 in the name of Andres Jaramillo-Boteo. date issued: Dec. 12, 2014.
Aksimentiev, A., et al., Microscopic Kinetics of DNA Translocation through Synthetic Nanopores, Biophysical Journal 2004, 87: 2066-2097.
Büttiker, M., et al., Generalized many-channel conductance formula with application to small rings, Physical Review B 1985, 31: 6207-6215.
Büttiker, M., et al., Magnetic field asymmetry in the multichannel Landauer formula, J. Phys. C: Solid State Phys. 1985, 18: L467-L472.
Chang, H., et al., DNA-Mediated Fluctuations in Ionic Current through Silicon Oxide Nanopore Channels, Nano Letters 2004, 4: 1151-1156.
Cornell, W., et al., A Second Generation Force Field for the Simulation of Proteins, Nucleic Acids, and Organic Molecules, J. Am. Chem. Soc. 1995, 117: 5179-5197.
Deng, WQ, et al., Bifunctional Anchors Connecting Carbon Nanotubes to Metal Electrodes for Improved Nanoelectronics, JACS 2007, 129: 9834-9835.
Deng, WQ, et al., An Electrochemical Color-Switchable RGB Dye: Tristable [2]Catenane, JACS 2007, 127: 15994-15995.
Deng, WQ, et al., Mechanism of the Stoddart-Heath Bistable Rotaxane Molecular Switch, JACS 2004, 126: 13652-13563.
Deng, WQ, et al., Computational simulation at molecular electronic and molecular electromechanical systems, Abstracts of Papers of the American Chemical Society 2003, 225: U708-U709.
Flood, A., et al., Meccano on the nanoscale—A blueprint for making some of the world's tiniest machines, Aust. J. Chem. 2004, 57: 301-322.
Harrison, DJ, et al., Micromachining a Miniaturized Capillary Electrophoresis-Based Chemical Analysis System on a Chip, Science 1993, 261: 895-897.
Heng, JB, et al., Stretching DNA Using the Electric Field in a Synthetic Nanopore, Nano Letters 2005, 5: 1883-1888.
Heng, JB, et al., The Electromechanics of DNA in a Synthetic Nanopore, Biophyiscal Journal 2006, 90: 1098-1106.
Kasianowicz, JJ, et al. Characterization of individual polynucleotide molecules using a membrane channel, pnas 1996, 93: 13770-13773.
Kim, YH, et al., Possible performance improvement in [2]catenane molecular electronic switches, Applied Physics Letters 2006, 88: 163112-1-163112-3.
Matsuda, Y., et al., Improving Contact Resistance at the Nanotube-Cu Electrode Interface Using Molecular Anchors, J. Phys. Chem. C 2008, 112: 11042-11049.

(56) References Cited

OTHER PUBLICATIONS

Matsuda, Y., et al., Contact resistance properties between nanotubes and various metals from quantum mechanics, J. Phys. Chem. C 2007, 111: 11113-11116.

Mayo, S., et al., Dreiding: A generic force field for molecular simulations, J. Phys. Chem. 1990, 94:8897-8909.

Merchant, CA, et al., DNA translocation through graphene nanopores, Nano Letters 2010, 10: 2915-2921.

PCT International Search Report mailed on Feb. 26, 2013 issued for PCT Application PCT/US2012/055787 filed on Sep. 17, 2012 in the name of California Institute of Technology et al.

PCT Written Opinion mailed on Feb. 26, 2013 issued for PCT Application PCT/US2012/055787 filed on Sep. 17, 2012 in the name of California Institute of Technology et al.

PCT International Search Report mailed on Feb. 26, 2013 issued for PCT Application PCT/US2012/055796 filed on Sep. 17, 2012 in the name of California Institute of Technology et al.

PCT Written Opinion mailed on Feb. 26, 2013 issued for PCT Application PCT/US2012/055796 filed on Sep. 17, 2012 in the name of California Institute of Technology et al.

Polonsky, S., et al., Nanopore in metal-dielectric sandwich for DNA position control, Applied Physics Letters 2007, 91: 153103-1-153103-3.

Postma, HW, Rapid sequencing of individual DNA molecules in graphene nanogaps, Nano Letters 2010, 10: 420-425.

Simpson, PC, et al., High-throughput genetic analysis using microfabricated 96-sample capillary array electrophoresis microplates, PNAS 1998, 95: 2256-2261.

Vercoutere, WA, et al., Discrimination among individual Watson-Crick base pairs at the termini of single DNA hairpin molecules, Nucleic Acids Research 2003, 31: 1311-1318.

Wendel, JA, et al., The Hessian biased force field for silicon nitride ceramics: Predictions of thermodynamic and mechanical properties for $\alpha$- and $\beta$-$Si_3N4$, J. Chem. Phys. 1992, 97: 5048-5062.

Winters-Hilt, et al., Highly Accurate Classification of Watson-Crick Basepairs on Termini of Single DNA Molecules, Biophysical Journal 2003, 84: 967-976.

Woolley, At, et al., Ultra-high-speed DNA sequencing using capillary electrophoresis chips, Anal. Chem. 1995, 67: 3676-3680.

Yam, Cy, et al., Dynamic admittance of carbon nanotube-based molecular electronic devices and their equivalent electric circuit, nanotechnology 2008, 19: 495203-1-495203-7.

\* cited by examiner

USING A FIELD EFFECT DEVICE FOR IDENTIFYING TRANSLOCATING CHARGE-TAGGED MOLECULES IN A NANOPORE SEQUENCING DEVICE

CROSS REFERENCE TO RELATED APPLICATIONS

The present application claims priority to U.S. Provisional Application 61/536,327 filed on Sep. 19, 2011, entitled "ssDNA Translocation Control and Nucleotide Sequencing Nano-Device Mechanisms" and U.S. Provisional Application 61/536,381 filed on Sep. 19, 2011, entitled "ssDNA Translocation Control and Nucleotide Sequencing Nano-Device Mechanisms", both of which are incorporated herein by reference. The present application is also related to U.S. patent application Ser. No. 13/621,735 filed on even date herewith, entitled "Translocation and Nucleotide Reading Mechanisms for Sequencing Nanodevices", which is also incorporated herein by reference.

FIELD

The present teachings relate to detection devices that may be used in connection with charge-tagged molecules translocating through a nanopore. More specifically, the present disclosure relates to detection devices that can be used for identification of nucleic acid sequences in charge-tagged DNA/RNA molecules.

BACKGROUND

Inexpensive and time-efficient full genome sequencing will enable prediction and impact-minimization of diseases through personalized, preventive medicine. Full genome sequencing is clearly of great importance for research into the basis of genetic disease. For example, access to a large database of individualized genome sequences will facilitate cross-correlating gene-type to gene-function.

However, full-genome sequencing with current technologies (e.g. chemical- or enzymatic-based shot-gun DNA sequencing, including massively parallel automated sequencers based on slab gel separation or capillary electrophoresis) is inadequate both in terms of performance and also in terms of cost.

SUMMARY

According to a first aspect of the present disclosure, a detector apparatus includes a membrane and a first field effect transistor. The membrane contains a nanopore and the first field-effect transistor is configured to undergo a change in amplitude of a source-to-drain current when at least a portion of a charge-tagged molecule translocates through the nanopore.

According to a second aspect of the present disclosure, a detector apparatus includes a field-effect transistor and a solid-state membrane. The field-effect transistor has a planar gate terminal, and the semiconductor layer has a nano-channel with a first portion of the nano-channel abutting a major surface of the planar gate terminal.

According to a third aspect of the present disclosure, a method of detection includes: a) forming a charge-tagged molecule, b) propagating the charge-tagged molecule through a nanopore of a membrane, and c) detecting a first amplitude of a source-to-drain current in a first field effect transistor, the first amplitude indicative of at least one charge tag in the charge-tagged molecule modifying an electrostatic potential of a gate portion of the first field-effect transistor.

Further aspects of the disclosure are shown in the specification, drawings and claims of the present application.

BRIEF DESCRIPTION OF THE DRAWINGS

The accompanying drawings, which are incorporated into and constitute a part of this specification, illustrate one or more embodiments of the present disclosure and, together with the description of a few example embodiments, serve to explain the principles and implementations of the disclosure. The components in the drawings are not necessarily drawn to scale. Instead, emphasis is placed upon clearly illustrating various principles. Moreover, in the drawings, like reference numerals designate corresponding parts throughout the several views.

DETAILED DESCRIPTION

Throughout this description, embodiments and variations are described for the purpose of illustrating uses and implementations of the inventive concept. The illustrative description should be understood as presenting examples of the inventive concept, rather than as limiting the scope of the concept as disclosed herein.

The various embodiments described herein are generally directed at using realizable solid-state membranes, more specifically realizable silicon nitride semiconductor membranes having nanopores. One or more field effect transistors (FETs) are located near one or more nanopores and the FETs are used to detect charge-tagged molecules that are propagated through the nanopores by using an ionic current.

The FETs used for this purpose are sized and structured differently from conventional FETs. More specifically, the source-to-drain current ($I_{DS}$ current) in a conventional FET is typically controlled by changing the dimension of a conducting channel located between the source and drain terminals.

This change in dimension is carried out by applying a voltage to a gate region of the FET via a gate terminal provided in the form of a metal contact. As can be understood, the size of the conducting channel is proportional to the length and the width of the gate region. The width may be selected to be much larger than the length, in order to provide amplification of a signal applied to the source terminal of the device. Furthermore, while the width limits the current carrying capacity and electrostatics sensitivity of the device, the length of the gate region limits the upper switching frequency of the device.

In contrast to the sizing and structure of a conventional FET, the FETs used in accordance with the present disclosure are miniature sized devices achieved by using carbon nanotubes (CNTs).

Carbon nanotube FETs (CNTFETs) have been built and demonstrated by various entities. For example, attention is drawn to a paper by Wind et al (reference [5]), which describes a CNTFET incorporating top gate electrodes. However, a CNTFET adapted for various embodiments in accordance with this present disclosure contains a modified gate region. More specifically, a CNTFET in accordance with the present disclosure is structured such that the source-drain current ($I_{DS}$ current) is controlled by charges present external to the CNTFET in the vicinity of the gate region, thereby dispensing with the conventional gate terminal (metal contact for providing the gate voltage). The structural basis and use of this CNTFET in accordance with the present disclosure will be described below in more detail using the various figures.

Figure 1:
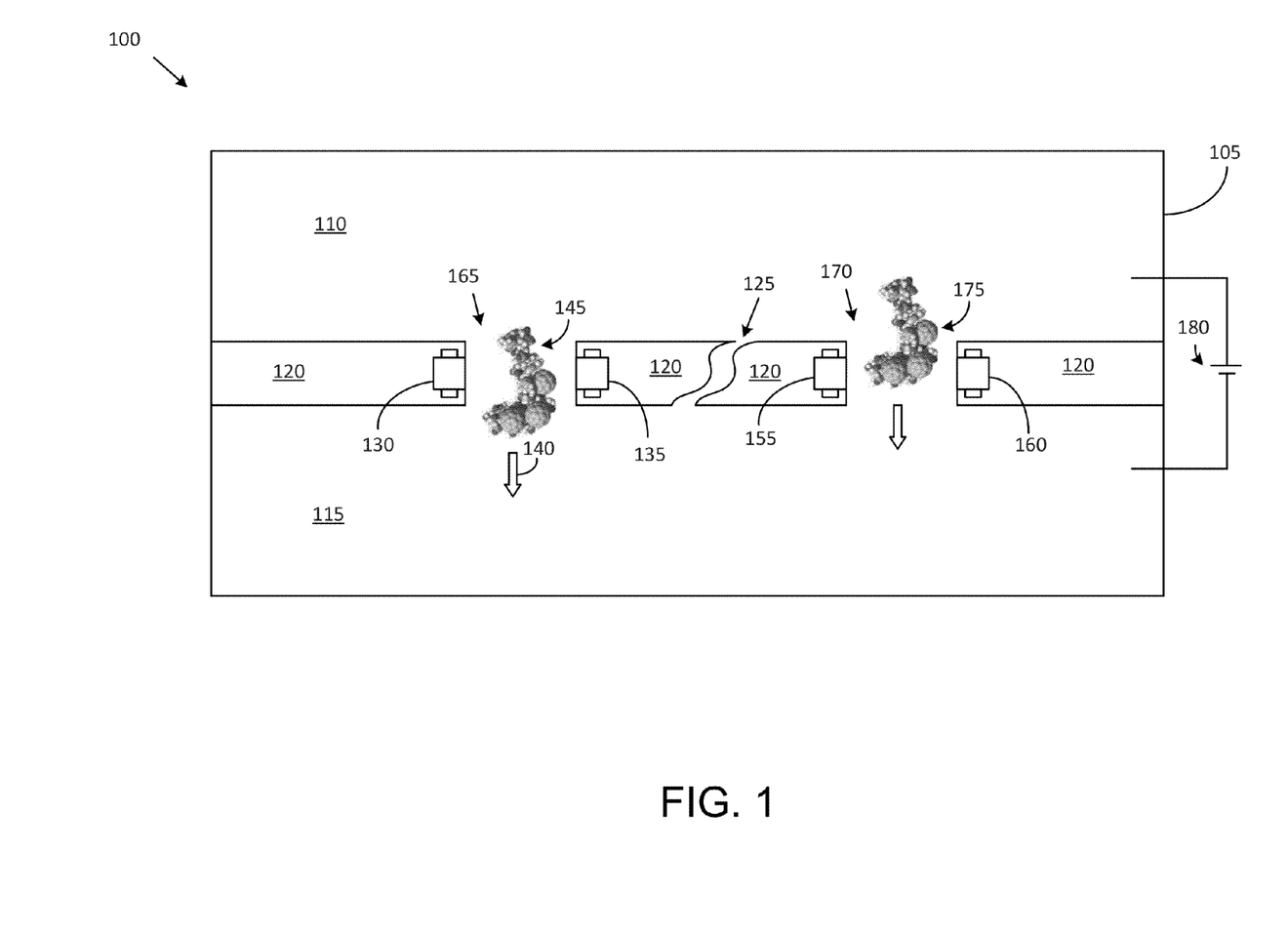
FIG. 1 shows a detection apparatus for detecting charge-tagged DNA molecules propagating through nanopores of a membrane in accordance with a first embodiment of the present disclosure.

Attention is first drawn to FIG. 1, which shows a detection apparatus 105, which may be alternatively referred to herein as a nanopore sequencing device, for detecting charge-tagged molecules propagating through nanopores 165 and 170 of a membrane 120 in accordance with a first example embodiment of the present disclosure. Detection apparatus 105 contains an upper reservoir 110 and a lower reservoir 115 with a membrane 120 disposed between the two reservoirs. Membrane 120 contains several nanopores (only two of which are shown in FIG. 1 for convenience). Reservoirs 110 and 115 contain a solution, such as for example, a mixture of water and potassium chloride (KCl), which is conducive to generating an ionic current upon application of a suitable voltage via a voltage source 180.

When the ionic current is generated, charge-tagged species, such as charge-tagged DNA molecules 145 and 175, propagate through nanopores 165 and 170 respectively of the nanopore sequencing device.

Charge-tagged DNA molecules can be generated in a variety of ways. For example, oligonucleotide charge-tags may be implemented via solid-phase synthesis using a phosphoramidite method (as disclosed in reference [4]) and phosphoramidite building blocks derived from protected 2'-deoxynucleosides (dA, dC, dG, and T), ribonucleosides (A, C, G, and U), or chemically modified nucleosides. Oligonucleotides between 16-28 bases long may be obtained by sequentially coupling the building blocks to the growing oligonucleotide chain in the order required by the sequence of the product. In accordance with various embodiments of the present disclosure, only the net charge of the oligonucleotide is used. Consequently, it is desirable to minimize the radius of gyration and choose a sequence based on partial complementarity along the chain so as to enable formation of looped structures with one exposed end having a minimum of 3-4 bases free for stable binding to a single-strand DNA (ssDNA) backbone. Having 3-4 bases free translates to a total of 64-256 different oligonucleotide combinations. The product of the solid-state synthesis is then released from the solid phase to a ssDNA solution, deprotected, and collected. The prepared oligonucleotides diffusively bind in solution to complementary codons in the ssDNA/RNA to form the charge tags.

Turning now to nanopores 165 and 170 contained in membrane 120, it may be pertinent to point out that only nanopore 165 and associated elements have been referred to in the description below. However, it should be understood, that the description is equally applicable to other similar nanopores and associated elements. (In this context, attention is drawn to jagged break 125 that is indicative of membrane 120 containing a larger area and more nanopores).

Nanopore 165 is populated with two CNTFETs 130 and 135 that are shown located inside membrane 120 and diametrically opposed to each other with respect to nanopore 165. Each of the two CNTFETs 130 and 135 operate as low dielectric constant FETs in a solvated environment (ionic solution).

A substantial portion of the gate of each of CNTFETs 130 and 135 is oriented parallel to a direction of flow of molecule 145 (indicated by arrow 140) and exposed to the nano channel. The amplitude of a source-to-drain current ($I_{DS}$ current) flowing in each of the two devices is modified when molecule 145 is located in proximity to the gate portions. In one embodiment, the $I_{DS}$ current increases when the tagged-charge present in molecule 145 is proximally located to the gate region of either CNTFET. Further details pertaining to detection apparatus 105 will be provided using other figures.

Figure 2:
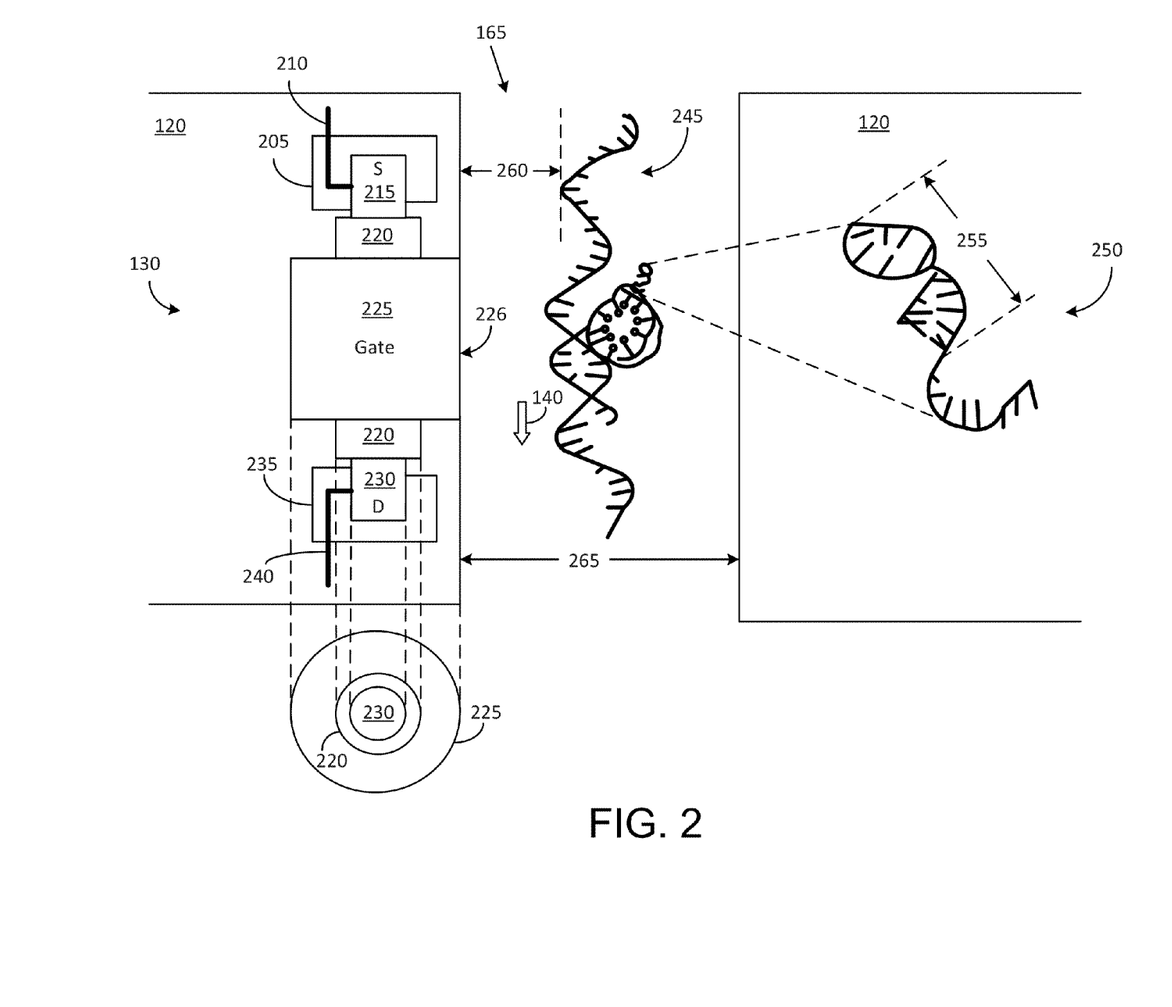
FIG. 2 shows some details of a carbon nanotube FET (CNTFET) that is a part of the detection apparatus in accordance with the present disclosure.

FIG. 2 shows additional details of CNTFET 130 that is shown in FIG. 1. It will be understood that in certain applications such as the one shown in FIG. 2, a single CNTFET 130, will be used, whereas in other applications CNTFET 130 will be used in conjunction with one or more additional CNTFETs such as CNTFET 135 shown in FIG. 1. The use of multiple CNTFETs provides various advantages such as, for example, increased detection sensitivity, redundant operation, and error checking features.

CNTFET 130 includes a gate portion 225 having a major surface 226 arranged in parallel to the direction of propagation 140 of a charge-tagged molecule, which in this example, is a charge-tagged single-strand DNA (ssDNA) molecule 245. In other implementations, the charge-tagged molecule may be other molecules, such as for example, charge-tagged RNA molecules. The charge-tagged ssDNA molecule 245 has a 3 to 4 base oligomer-ssDNA complementarity that provides thermodynamic stability to the complex, particularly using locked nucleic acid (LNAs as described in references [6] and [7]) oligomers. Oligonucleotide 250 includes a hairpin length 255 that determines the charge.

Gate portion 225 comprises a dielectric material such as a polysilicon, which is wrapped around a carbon nanotube portion 220. The CNTFET 130 further includes a source portion 215, a source pad 205, a drain portion 230, and a drain pad 235. Source-to-drain biasing may be provided by applying a $U_{DS}$ voltage (not shown) via terminals 210 and 240 that are connected to source portion 215 and drain portion 230 respectively. The $U_{DS}$ voltage sets up a quiescent current flow between the source and drain portions. This quiescent current is modified in amplitude when charge-tagged single-strand DNA (ssDNA) 245 is in proximity to gate portion 225 when propagating through nanopore 165.

The proximity parameter is determined in part by selecting a suitable diameter 265 of the nanopore 165. In one example embodiment, diameter 265 is selected not to exceed 3 nm. Diameter 265 may be alternatively viewed as a contributory factor for a separation distance 260 between major surface 226 and charge-tagged single-strand DNA (ssDNA) 245 that is translocating through nanopore 165. In one example embodiment, separation distance 260 is about 2 nm.

The fabrication of CNTFET 130 may be carried out via a number of techniques. In one approach, semiconducting single-walled carbon nanotubes are used because such devices provide certain advantages (such as faster switching properties at low source/drain voltages) over metallic single-walled and metallic multi-walled tubes. The silicon-based fabrication of nanopores may be carried out via processes such as described in reference [1]. The fabrication process described in reference [1] may be modified to include additional steps that include incorporating CNTFET 130 within or outside membrane 120.

In general, the fabrication process may begin with building a wrap-around CNTFET (preferred over top-gated devices like the one disclosed in reference [5]) since the wrap-around CNTFET provides an improved device on/off ratio. The wrapping is carried out using a dielectric material that is wrapped around the entire length of the CNTFET. The CNTFET is then placed upon membrane 120 and a portion of the wrapping is removed (for example, by etching) so as to expose the extremities of carbon nanotube portion 220. Source, drain, and gate contacts may then be provided. A focused electron beam may be used to create one or more 2-3 nm nanopores in membrane 120. The nanopore fabrication process may be carried out as disclosed in reference [1]. Then one or more CNTFETs are incorporated into or on membrane 120. In the FIG. 1 embodiment, the nanopore is created between the two CNTFETs.

Figure 3:
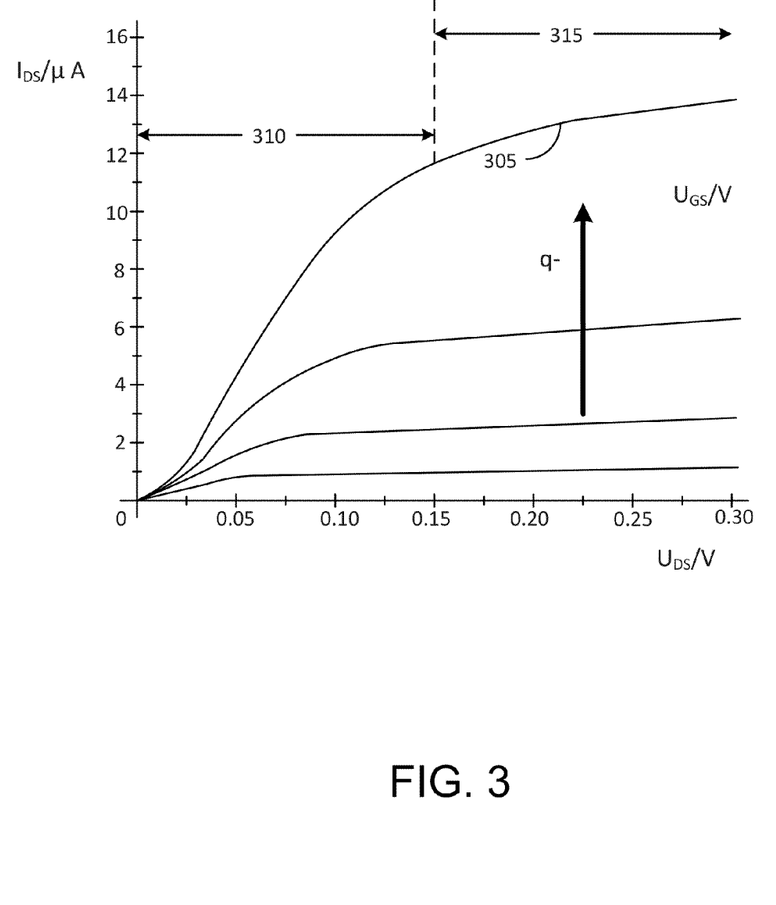
FIG. 3 shows the effect of changes in charge-tag magnitudes on a drain-to-source current-voltage (I-V) characteristic graph of a CNTFET in accordance with the present disclosure.

Attention is now drawn to FIG. 3, which shows the effect of changes in charge-tag magnitudes on a drain-to-source current-voltage (I-V) characteristic of a CNTFET in accordance with the present disclosure. Each of the curves represent gate-to-source voltages ($U_{GS}$) corresponding to various gate charges (q–). Using curve 305 for purposes of explanation, it can be observed that curve 305 includes a substantially linear rising portion 310 (where $I_{DS}$ rises substantially linearly in correspondence to an increase in $U_{DS}$ the drain-to-source voltage); and a substantially flat portion 315 (where the $I_{DS}$ remains substantially constant upon increase in $U_{DS}$). The linear rising portion 310 corresponds to a linear mode of operation of detection apparatus 105 and it is this linear mode of operation that is used in the various embodiments in accordance with the present disclosure. The substantially flat portion 315, which corresponds to a saturated region of operation, is not typically used when identifying translocating charge-tagged molecules.

The linear mode of operation is used so as to enable identification and detection of the 64-256 different free end oligonucleotide combinations that correspond to the 3-4 bases which are free to bind stably to a backbone complementary sequence of bases of a ssDNA molecule. Each of the 64-256 combinations generates a uniquely identifiable change in $I_{DS}$ current in a CNTFET. In contrast, the saturated mode of operation would be unsuitable for use in detecting these various combinations because $I_{DS}$ would remain relatively constant for the various combinations. However, the saturated region of operation may be utilized in various other applications in accordance with the disclosure that support a CNTFET on-off switching mode of operation.

Figure 4:
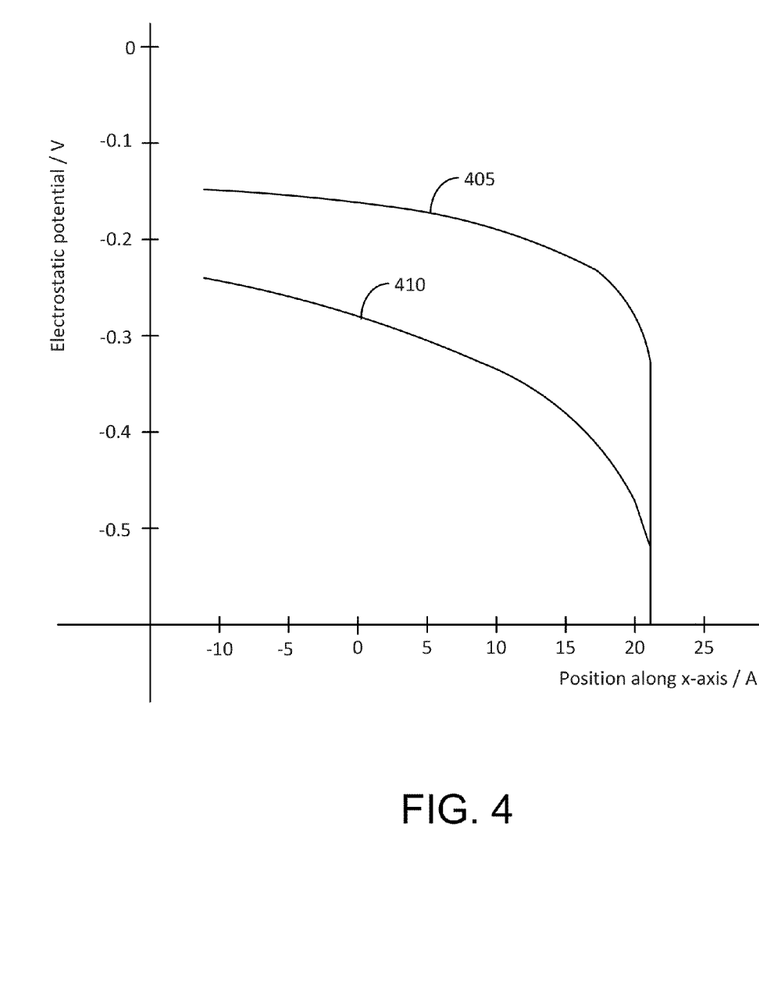
FIG. 4 shows a graph of electrostatic potential with and without the charge tag contribution from a 10-base charge-tagged ssDNA oligomer at various distances from a gate portion of a CNTFET.

FIG. 4 shows a graph of electrostatic potential versus charge tag contribution from a 10-base oligomer charge-tagged ssDNA at various distances ("r") from a CNTFET gate.

Curve 410 indicates the total electrostatic potential without a charge-tag and curve 405 indicates the changed electrostatic potential due to the presence of a 10-base oligonucleotide charge-tag as a function of varying distances (r) from a CNTFET gate. At r=1 nm the charge tag is a few tenths of a Volt, sufficient to activate $I_{DS}$ current change in the CNTFET.

A predictive simulation involving a Non-Equilibrium Green's Function (NEGF) approach was used to compute the current-voltage (IV) and device conductance graph shown in FIG. 4. Carbon atoms were described using an extended Huckel model (as disclosed in reference [2]) with Cerda basis (reference [3]). For a 1.8 nm gate: a $V_{GD}$=−0.4V increases the nanotube resistance from 22.13-22.14 kΩ, and for a 0.9 nm gate $V_{GD}$=−0.4V increases nanotube resistance from 22.14-22.20 kΩ. Larger gating effect would lead to higher nucleic acid distinguishability in a nucleobase sequencing nanopore device.

In one quantum mechanical simulation using an explicit solvent model, charge-screening effects on the gate potential were predicted using short (~10 bases long) 3-base complementary oligomeric charge tags on specific ssDNA sequences. In this predictive quantum mechanical calculation, the detector apparatus remains operational within r<=~1 nm, and provides discriminatory electron current signatures $I_{SD}$ for different nucleic acid sequences with charge-tags differing by 2-4e.

Figure 5:
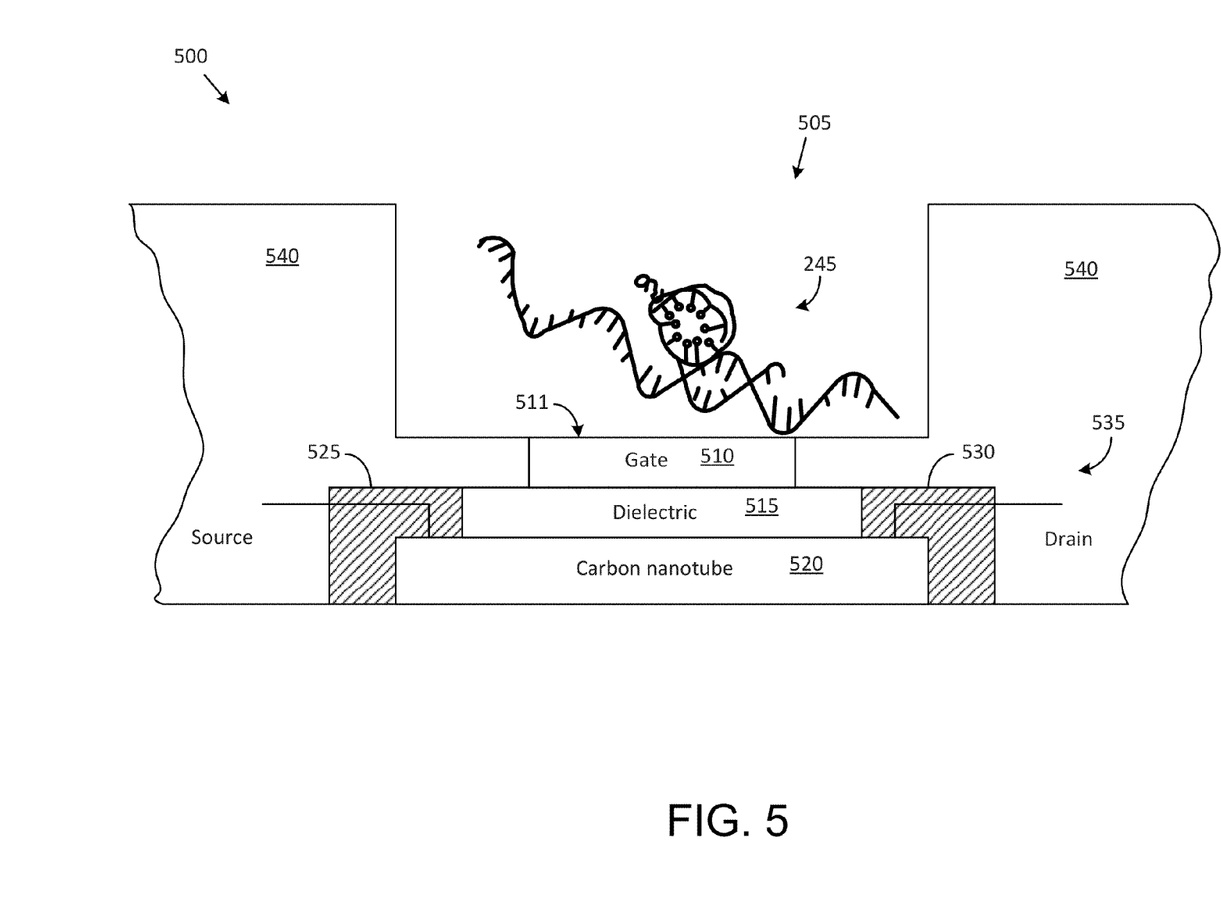
FIG. 5 shows a detection apparatus for detecting charge-tagged DNA molecules propagating through a nanopore in accordance with a second embodiment of the present disclosure.

FIG. 5 shows a detection apparatus 500 for detecting charge-tagged DNA molecules propagating through a nanopore in accordance with a second embodiment of the present disclosure. In this embodiment, CNTFET 535 has a planar configuration that may be fabricated using semiconductor fabrication techniques. CNTFET 535 includes a carbon nanotube portion 520, a dielectric portion 515, a source portion 525, a drain portion 530, and a gate portion 510 having a major surface 511 abutting a channel 505. Channel 505 is representative of a nanopore through which a charge-tagged molecule, such as charge-tagged single-strand DNA (ssDNA) 245, is translocated using an ionic solution. Channel 505 may be fabricated in the form of a groove in a semiconductor layer 540, with a longitudinal axis of the groove projecting out of the plane of the paper on which FIG. 5 is drawn. It will therefore be understood that charge-tagged single-strand DNA (ssDNA) 245 translocates along this longitudinal axis, or in other words in a direction that may be viewed as emerging out of the drawing sheet on which FIG. 5 is drawn.

Furthermore, it will be understood that though channel 505 is shown in FIG. 5 as having a rectangular cross-section, various other cross-sectional configurations such as a circular cross-section, may be used instead. Generally, the cross-section is selected so as to provide an interaction region with gate 510 whereby a charge-tagged molecule propagating through the nanopore has an effect on the $I_{DS}$ current flow in CNTFET 535.

Figure 7:
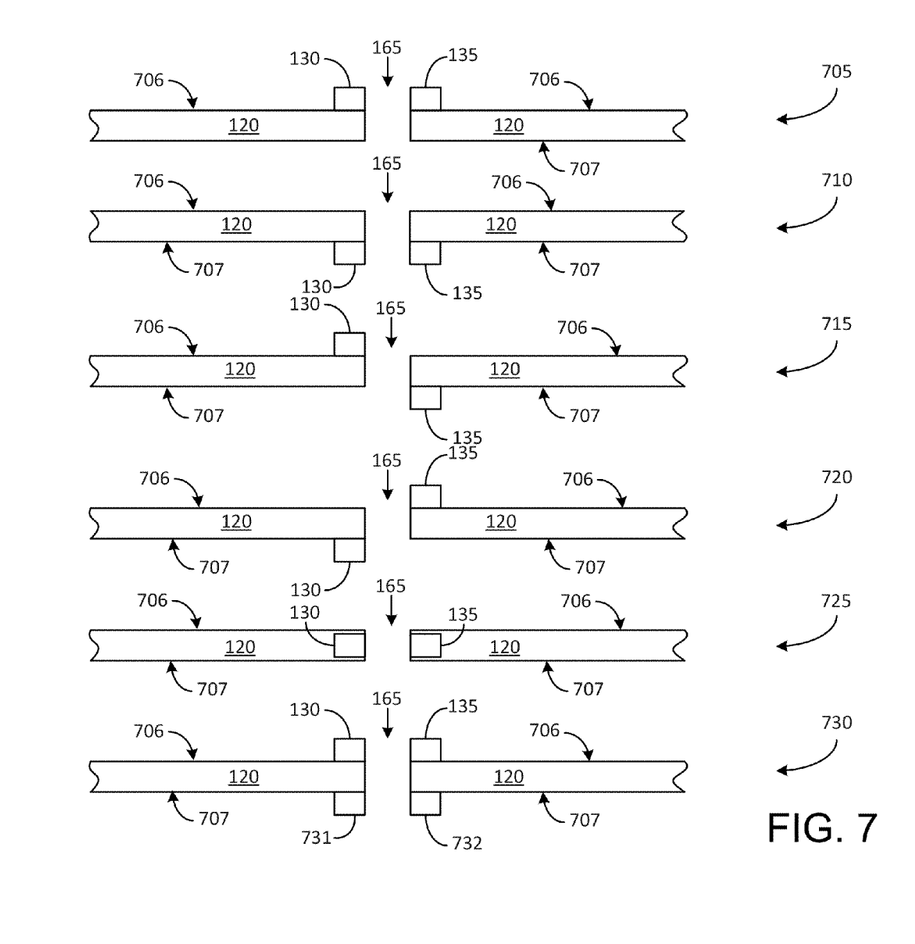
FIG. 7 shows various configurations for mounting a pair of CNTFETs upon a membrane in accordance with the present disclosure.

In a sixth configuration 730, four CNTFETs are used. Specifically, a first CNTFET 130 and a second CNTFET 731 are each located on opposing major surfaces 706 and 707 on one side of nanopore 165. A third CNTFET 135 and a fourth CNTFET 732 are each located on opposing major surfaces 706 and 707 on a diametrically opposite side of nanopore 165.

Figure 6:
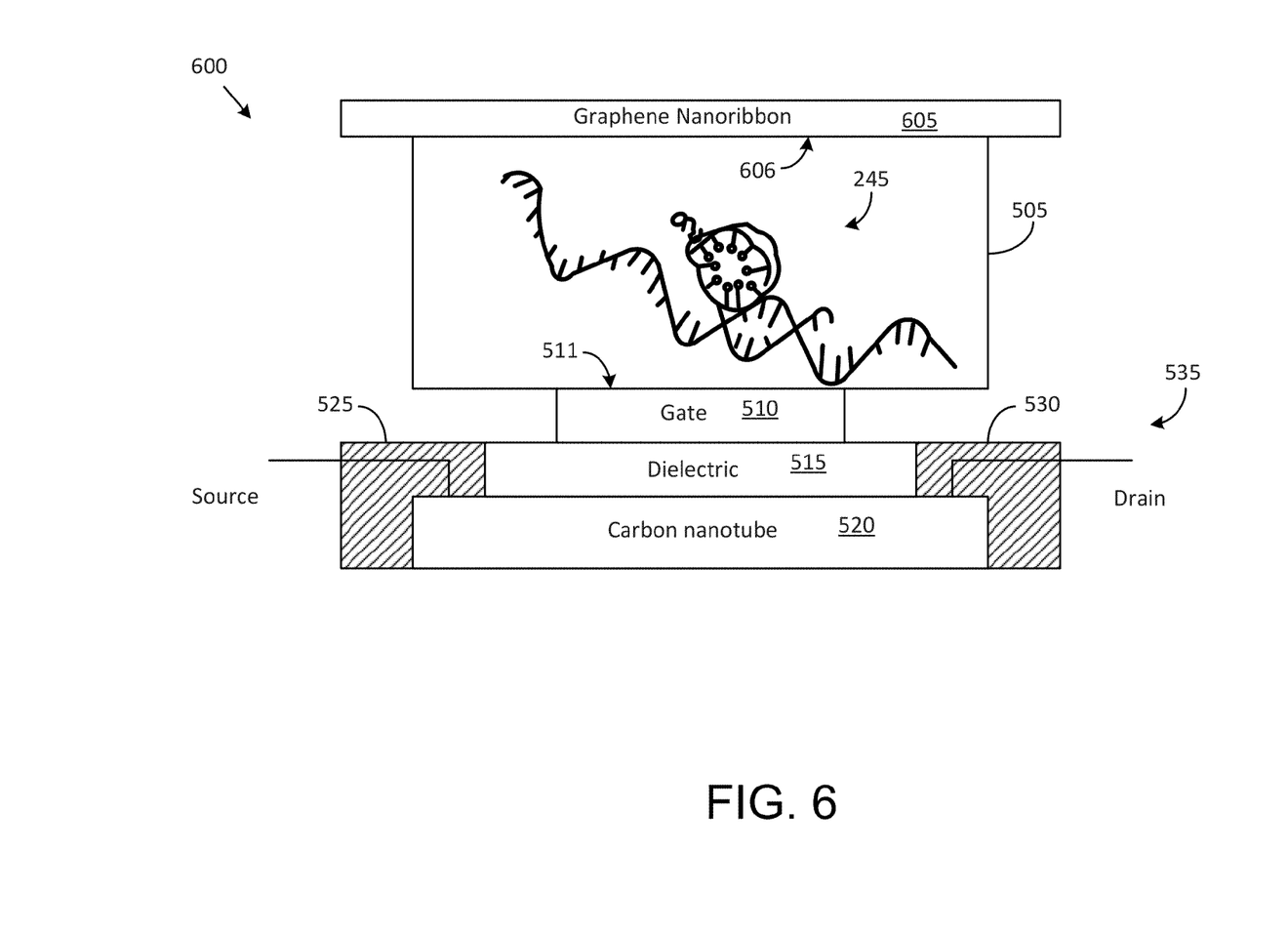
FIG. 6 shows a detection apparatus for detecting charge-tagged DNA molecules propagating through a nanopore in accordance with a third embodiment of the present disclosure.

In contrast, to the embodiment shown in FIG. 5 (wherein CNTFET 535 is used as a single detector for identifying charge-tagged molecules propagating through a nanopore), the third embodiment of a detector apparatus 600 shown in FIG. 6 incorporates two detectors.

The first detector is a CNTFET 535 that has been described above. The second detector is implemented in the form of a graphene nanoribbon layer 605 that abuts an opposing surface 606 of channel 505. Opposing surface 606 opposes major surface 511 described above. A quiescent current may be generated across the graphene nanoribbon 605 upon application of a suitable biasing voltage between the two ends laid on top of the silicon support 605 by using a suitable voltage source (not shown). This quiescent current is affected when a charge-tagged molecule propagates through nanopore 505. The change in current, which may be referred to herein as a sense current, is used to detect the various free end oligonucleotide combinations that may be present in a backbone of a charge-tagged ssDNA molecule propagating through nanopore 505.

FIG. 7 shows various configurations for mounting a pair of CNTFETs upon a membrane in accordance with the present disclosure. In a first configuration 705, a first CNTFET 130 is located upon a first major surface 706 of membrane 120 on one side of nanopore 165. A second CNTFET 135 is located upon the same first major surface 706 of membrane 120 but on a diametrically opposite side of nanopore 165.

In a second configuration 710, the first CNTFET 130 is located upon an opposing major surface 707 of membrane 120 on one side of nanopore 165. A second CNTFET 135 is located upon the same opposing major surface 707 of membrane 120 but on a diametrically opposite side of nanopore 165.

In a third configuration 715, the first CNTFET 130 is located upon a first major surface 706 of membrane 120 on one side of nanopore 165. A second CNTFET 135 is located upon the opposing major surface 707 of membrane 120 on a diametrically opposite side of nanopore 165.

In a fourth configuration 720, the second CNTFET 135 is located upon a first major surface 706 of membrane 120 on one side of nanopore 165. The first CNTFET 130 is located upon the opposing major surface 707 of membrane 120 on a diametrically opposite side of nanopore 165.

In a fifth configuration 725, one or more CNTFETs may be embedded inside membrane 120. (FIG. 1 shows several CNTFETs embedded in membrane 120). In one embodiment wherein one or more CNTFETs are embedded inside membrane 120, membrane 120 is selected to have a thickness 726 between 20-50 nanometers.

Figure 8:
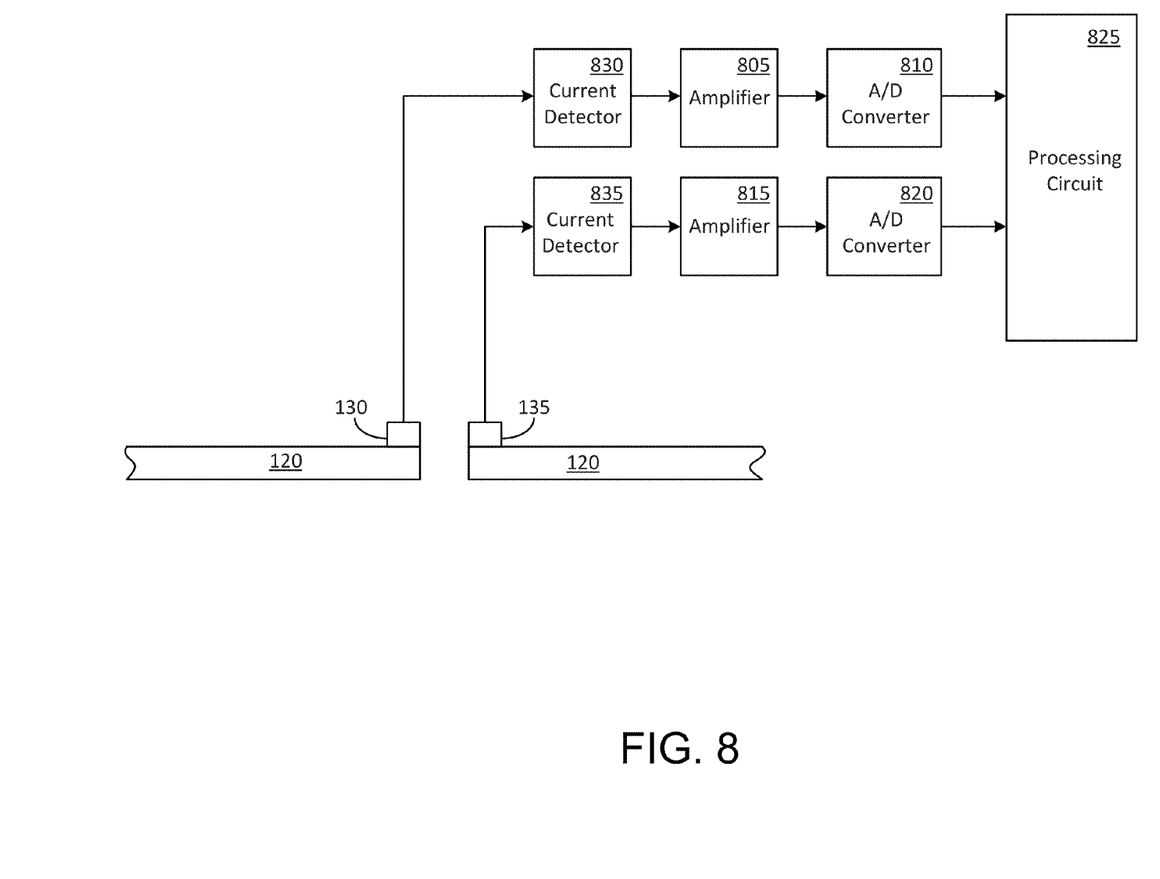
FIG. 8 shows additional elements that are coupled to a pair of CNTFETs for carrying out various types of processing operations upon data provided by the pair of CNTFETs.

FIG. 8 shows additional elements that are coupled to a pair of CNTFETs for carrying out various types of processing operations upon data provided by the pair of CNTFETs. More particularly, the $I_{DS}$ currents generated in CNTFETs 130 and 135, which may be a part of current detectors 830 and 835 respectively, are amplified in instrumentation amplifiers 805 and 810 for generating amplified voltage signals. The voltage signals generated in the two amplifiers are provided to a pair of analog-to-digital converters (ADCs) 810 and 820. The digital signals generated by the pair of converters from the amplified voltage signals are provided to processing circuit 825, which processes the digital signals to obtain meaningful information. Processing circuit 825 includes various elements (not shown) such as a processor, a computer-readable storage medium for storing data and/or software/firmware programs, and input/output interface elements.

It will be understood that the digital data provided to processing circuit 825 by ADCs 810 and 820, may be used for implementing various features in accordance with the present disclosure, such as redundant operations, error-correction operations, and/or parallel processing operations. For example, in a redundant mode of operation, a failure in one of the two CNTFETs may be addressed by ignoring the failed CNTFET and using only the one operational CNFT. In an error-correction mode of operation the digital data provided by the two CNTFETs may be compared against each other in order to ensure accuracy and robustness of operation. In parallel processing operations, the $I_{DS}$ currents generated by two or more CNTFETs 130 and 135 may be used to derive a variety of information pertaining to a single charge-tagged molecule, or multiple charge-tagged molecules that may be concurrently or sequentially propagating through a nanopore.

Furthermore, while FIG. 8, shows CNTFETs 130 and 135 in a detection configuration corresponding to the first embodiment described above, the processing operations and elements described using FIG. 8 are equally valid for various other embodiments (for example, the embodiment shown in FIG. 6) wherein a pair of CNTFETs are employed.

Turning away from FIG. 8, attention is once again drawn to FIG. 2. The interaction between CNTFET 130 and charge-tagged single-strand DNA (ssDNA) 245 may be calculated by assuming a minimized gate capacitance (i.e. A and $\in_0 \in_r$ in the following equation for gate capacitance: $C=\in_0 \in_r A/r$, where "r" is the separation distance 260); an estimated Coulomb interaction effect (for example, from water) via expressing the contribution to the E-field at a point in space (CNTFET gate surface) due to a single, discrete point charge (ne, from charge species) located at another point in space, distanced by r, results in an electrical potential of >=0.9V for r<=2 nm. This calculation also assumes: discrete water molecules in the nanopore have a dielectric constant dominated by their orientation (large dipole moment), stronger screening effects in (K+) ionic solution (the negatively charged ssDNA backbone and negative charge-tags attract positive counter ions), and that the complex appears neutral from distance larger than the backbone-counter ion distance (although the nanopore may strip ions from ssDNA backbone during translocation) to determine a worst case scenario for operating the CNTFET device in the linear mode of operation.

A test model comprising a nanotube (m=5, n=0, length=4.3 nm), left and right metallic electrodes, a dielectric region (with dielectric constant 4) separating the nanotube and the gate, and a gate bias voltage was used to assess performance of a modeled embodiment of the present disclosure. The gate size was selected to be approximately 1.2×1.2 nm, which approximates to the electric field of a point charge. Assuming a charge-tag with 20e (i.e. 20 nucleotides long), a small nanopore (1.5-2.5 nm) capable of stripping counter ions from the charge-tag, and a distance of approximately 1 nm between the charge-tag and a CNTFET gate insulator surface leads to a potential at the insulator of −0.4V (screened Coulomb).

In conclusion, a detector apparatus in accordance with the present disclosure enables sufficiently small charge tags (for example, 8-136 bases, considering a 3-base complementary overlap between charge tag and ssDNA) on ssDNA to gate-activate a CNTFET in a linear mode of operation. The detector apparatus preferably has a device sensitivity that enables detection of small tags with 2-4e potential difference at distances ~1 nm in a solvated environment (ionic solution described above).

All patents and publications mentioned in the specification may be indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The examples set forth above are provided to give those of ordinary skill in the art a complete disclosure and description of how to make and use the embodiments of the terrain traversal device of the disclosure, and are not intended to limit the scope of what the inventors regard as their disclosure. Modifications of the above-described modes for carrying out the disclosure may be used by persons of skill in the robotic arts, and are intended to be within the scope of the following claims.

A number of embodiments of the disclosure have been described. Nevertheless, it will be understood that various modifications may be made without departing from the spirit and scope of the present disclosure. Accordingly, other embodiments are within the scope of the following claims.

LIST OF REFERENCES

1. Dekker, C., *Solid-state nanopores*. Nature Nanotechnology, 2007. 2(4): p. 209-215.
2. Stokbro, K., et al., Semiempirical model for nanoscale device simulations. Physical Review B, 2010. 82(7).
3. Cerda, J. and F. Soria, Accurate and transferable extended Huckel-type tight-binding parameters. Physical Review B, 2000. 61(12): p. 7965-7971.
4. Beaucage, S. L. and M. H. Caruthers, Deoxynucleoside Phosphoramidites—a New Class of Key Intermediates for Deoxypolynucleotide Synthesis. Tetrahedron Letters, 1981. 22(20): p. 1859-1862.
5. Wind, S. J., et al., Vertical scaling of carbon nanotube field-effect transistors using top gate electrodes (vol 80, pg 3817, 2002). Applied Physics Letters, 2002. 81(7): p. 1359-1359.
6. Singh, S. K., et al., LNA (locked nucleic acids): synthesis and high-affinity nucleic acid recognition. Chemical Communications, 1998(4): p. 455-456.
7. Koshkin, A. A., et al., LNA (Locked Nucleic Acids): Synthesis of the adenine, cytosine, guanine, 5-methylcytosine, thymine and uracil bicyclonucleoside monomers, oligomerisation, and unprecedented nucleic acid recognition. Tetrahedron, 1998. 54(14): p. 3607-3630.

What is claimed is:

1. A detector apparatus comprising:
a membrane containing a nanopore; and
first and second wrap-around carbon nanotube field-effect transistors configured to undergo a change in amplitude of a source-to-drain current when at least a portion of a charge-tagged molecule translocates through the nanopore,
wherein:
the nanopore has a nanopore longitudinal axis parallel to a direction of propagation of the at least a portion of the charge-tagged molecule translocating through the nanopore,
the first wrap-around carbon nanotube field-effect transistor has a first transistor longitudinal axis parallel to the nanopore longitudinal axis,
the second wrap-around carbon nanotube field-effect transistor has a second transistor longitudinal axis parallel to the nanopore longitudinal axis, and
the first and second wrap-around carbon nanotube field effect transistors are arranged on diametrically opposing edges of the nanopore for substantially concurrently detecting the at least a portion of the charge-tagged molecule translocating through the nanopore.

2. The apparatus of claim 1, wherein a diameter of the nanopore is selected to provide a separation distance not exceeding 2 nm between the major surface gate portion of the first carbon nanotube field effect transistor and the at least a portion of the charge-tagged molecule translocating through the nanopore.

3. The apparatus of claim 2, wherein the diameter of the nanopore does not exceed 3 nm.

4. The apparatus of claim 3, further comprising a reservoir containing an ionic solution, the reservoir configured for electrophoretically translocating the at least a portion of the charge-tagged molecule through the nanopore.

5. The apparatus of claim 4, wherein the reservoir comprises two compartments and the membrane is arranged therebetween whereby the at least a portion of the charge-tagged molecule translocates through the nanopore from one to the other of the two compartments.

6. The apparatus of claim 5, wherein first carbon nanotube field effect transistor is located in one of: a) inside the membrane, b) on a major surface of the membrane, or c) on an opposing major surface of the membrane.

7. The apparatus of claim 5, wherein the membrane is a silicon nitride semiconductor membrane having a thickness of 20-50 nanometers and a plurality of nanopores.

8. The apparatus of claim 1, wherein the membrane has a thickness range of 20-50 nm, and wherein the first and second carbon nanotube field effect transistors are located in one of: a) inside the membrane, b) on a major surface of the membrane, or c) on opposing major surfaces of the membrane.

9. The apparatus of claim 4, wherein the first carbon nanotube field effect transistor is configured to operate in a linear mode of operation for identifying one or more oligonucleotide combinations contained in the at least a portion of the charge-tagged molecule.

* * * * *